United States Patent [19]
Gao et al.

[11] Patent Number: 6,113,993
[45] Date of Patent: Sep. 5, 2000

[54] METHOD OF COATING A SUBSTRATE WITH A CALCIUM PHOSPHATE COMPOUND

[75] Inventors: Yufei Gao; Allison A. Campbell, both of Kennewick, Wash.

[73] Assignee: Battelle Memorial Institute, Richland, Wash.

[21] Appl. No.: 09/182,741

[22] Filed: Oct. 28, 1998

[51] Int. Cl.$^7$ .................... H05H 1/24; B05D 3/00
[52] U.S. Cl. .............. 427/573; 427/2.27; 427/255.29; 427/255.31; 427/255.38; 427/575
[58] Field of Search .............. 427/2.27, 255.29, 427/255.38, 255.31, 314, 573, 575, 569

[56] References Cited

U.S. PATENT DOCUMENTS 5,441,536  8/1995  Aoki et al. .............................. 427/2.27

OTHER PUBLICATIONS

Allen et al, Nucl. Instrum. Methods Phys. Res., Sect. B., 116(1–4) p. 457–460, 1996.

BC Bunker, et al., Ceramic Thin–Film Formation on Functionalized Interfaces Through Biomimetic Processing, American Association for the Advancement of Science, Reprint series, Apr. 1, 1994, vol. 264, pp. 48–55.

AA Campbell, et al., Surface–induced mineralization: A new method for producing calcium phosphate coatings, Journal of Biomedical Materials Research, vol. 32, 111–118 (1996).

KA Thomas, PhD, Hydroxyapatite Coatings, Orthopedics, vol. 17, No. 3, pp. 267–277 (1994).

FZ Cui, et al., Highly adhesive hydroxyapatite coatings on titanium alloy formed by ion beam assisted deposition, Journal of Materials Science: Materials in Medicine, vol. 8, pp. 403–405, (1997).

*Primary Examiner*—Roy V. King
*Attorney, Agent, or Firm*—Paul W. Zimmerman

[57] ABSTRACT

The present invention is a method of coating a substrate with a calcium phosphate compound using plasma enhanced MOCVD. The substrate is a solid material that may be porous or non-porous, including but not limited to metal, ceramic, glass and combinations thereof. The coated substrate is preferably used as an implant, including but not limited to orthopaedic, dental and combinations thereof. Calcium phosphate compound includes but is not limited to tricalcium phosphate (TCP), hydroxyapatite (HA) and combinations thereof. TCP is preferred on a titanium implant when implant resorbability is desired. HA is preferred when the bone bonding of new bone tissue into the structure of the implant is desired. Either or both of TCP and/or HA coated implants may be placed into a solution with an agent selected from the group of protein, antibiotic, antimicrobial, growth factor and combinations thereof that can be adsorbed into the coating before implantation. Once implanted, the release of TCP will also release the agent to improve growth of new bone tissues and/or to prevent infection.

17 Claims, 2 Drawing Sheets ns with a calcium phosphate compound as an implant for bone or tooth or as an optical device.

METHOD OF COATING A SUBSTRATE WITH A CALCIUM PHOSPHATE COMPOUND

This invention was made with Government support under Contract DE-AC0676RLO1830 awarded by the U.S. Department of Energy. The Government has certain rights in the invention.

FIELD OF THE INVENTION

The present invention relates to a method of coating a substrate with a calcium phosphate compound as an implant for bone or tooth or as an optical device.

BACKGROUND OF THE INVENTION

Use of prosthetic implants for bone is rapidly increasing in the medical community. Orthopaedic prosthetic implants are commonly made of titanium (Ti) alloy because of its corrosion resistance to body fluids. However, Ti alloys do not form a direct bond with bone. It has been demonstrated that a calcium phosphate coating on the titanium enhances bone apposition to endosseous implants. It is believed that the calcium phosphate permits bone to bond to the coated prosthetic surface and thus enhances implant fixation. Hydroxyapatite (HA) ($Ca_5(PO_4)_3OH$) and tricalcium phosphate (TCP) ($Ca_3(PO_4)$) are particularly attractive materials for coating titanium for hard tissue implants in plastic surgery because of their capability of directly integrating to bone tissues by their resorption (e.g. TCP) or by facilitating bone bonding of newly forming bone into their structures (e.g. HA). Several methods have been used for applying the coating to the titanium including plasma spraying which is the most frequently used technique to produce HA coatings[1-3]. Other, less frequently used methods include solution deposition sometimes referred to as biomimetic process[2,4]. Present methods of making TCP or HA coatings result either in very porous coatings (less than 80% of theoretical density) from less than 1 micron to many microns thick, or in dense coatings (greater than or equal to 80% of theoretical density) by deposition of particles (thermo-spray)[1] which limits the thickness of the dense coating to be at least 5 micron.

In the technically unrelated field of semiconductor manufacture, plasma-enhanced metalorganic chemical vapor deposition (PEMOCVD) has been used for deposition of ceramic coatings of oxides and nitrides for semiconductor applications. (Calcium phosphate and hydroxyapatite are not used in semiconductor manufacture.) In the PEMOCVD process, a gaseous stream of metalorganic precursors containing the reactive constituents for the desired ceramic (oxide or nitride) coating material and a plasma are directed toward a heated semiconductor substrate, where the plasma ionizes and activates the gaseous stream and a reaction takes place to form a solid film or coating. Reaction byproducts are pumped out. The process is terminated when a desired coating thickness is obtained. PEMOCVD is known to be capable to produce uniform coatings on complex-shape substrates. More specifically, semiconductor manufacture uses PEMOCVD to deposit silicon oxide onto various layers of an electronic chip. PEMOCVD is also used in the semiconductor manufacture to deposit doped gallium arsenide and/or doped gallium nitride onto gallium arsenide or silicon for laser material.

Hence, there is a need in the manufacture of implants for a method of producing a thin and dense implant coating that is less expensive than present coating methods. There may also be a need in optical device manufacture for a method of coating the optical device.

BACKGROUND REFERENCES

1. Thomas, K A, Orthopedics 1994; 17: 267–278.
2. Campbell A A., Journal of Biomedical Materials Research, 1996, 32: 111–118.
3. Cui, F Z, Luo, Z S, Feng, Q L, J Mater. Sci.: Mater. In Medicine 1997; 8: 403–405.
4. B C Bunker, P C Rieke, B J Tarasevich, M Campbell, G E Fryxell, G L Graff, L Song, J Liu, J W Virden and G L McVay, *Ceramic Thin Film Formation on Functionalized Interfaces Through Biomimetic Processing*, Science, 264, 48–55 (1994).

SUMMARY OF THE INVENTION

The present invention is a method of coating a substrate with a calcium phosphate compound using PEMOCVD. The substrate is a solid material that may be porous or non-porous, including but not limited to metal, ceramic, glass and combinations thereof. The coated substrate is preferably used as an implant, including but not limited to orthopaedic, dental and combinations thereof.

Calcium phosphate compound includes but is not limited to tricalcium phosphate (TCP), hydroxyapatite (HA) and combinations thereof.

TCP is preferred on a titanium implant when implant resorbability is desired. Hydroxyapatite is preferred when bone bonding of new bone tissue into the structure of the implant is desired.

Either or both of TCP and/or HA coated implants may be placed into a solution with an agent selected from the group of protein, antibiotic, antimicrobial, growth factor and combinations thereof that can be adsorbed into the coating before implantation. Once implanted, the release of TCP will also release the agent to improve growth of new bone tissues and/or to present infection.

The present invention includes dense coatings that are less than 5 micron in thickness.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
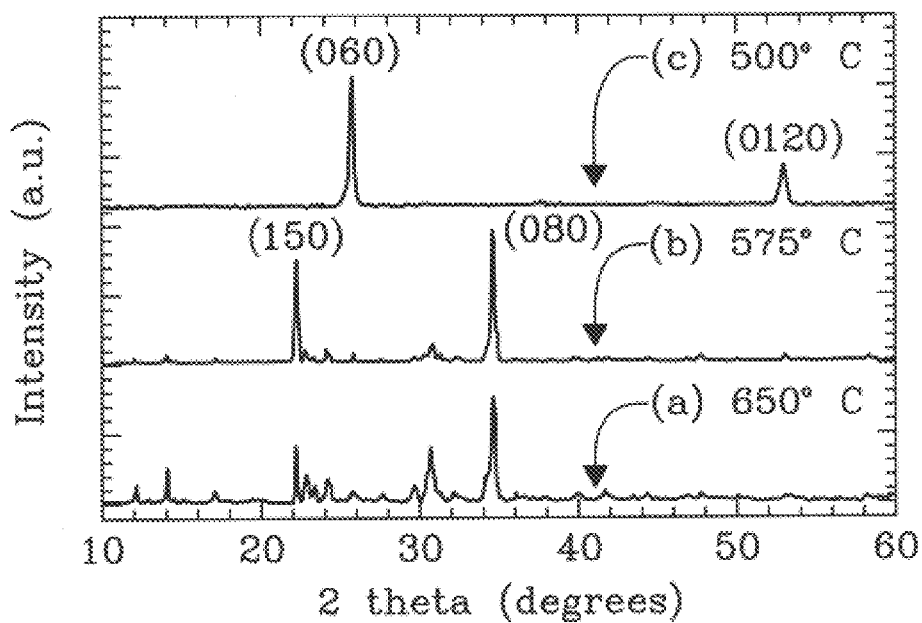
FIG. 1 is three X-ray diffraction patterns, one each for TCP coatings deposited at substrate temperatures of (a) 650° C., (b) 575° C. and (c) 500° C.

According to the present invention, the method of coating a substrate with a calcium phosphate compound relies upon the PEMOCVD process wherein (a) a gaseous stream of a mixture of coating precursors and an oxygen plasma are (b) directed toward a heated metal substrate, where a reaction takes place to form the calcium phosphate compound coating. Reaction byproducts are pumped out. The process is terminated when a desired coating thickness is obtained.

The substrate is a solid material of metal, ceramic, glass or combinations thereof. For orthopaedic and/or dental implants, the preferred substrate is metal, for example titanium, titanium alloy, chrome molybdenum steel, stainless steel and combinations thereof. The coated substrate may also be useful for an optical device, especially with a hydroxyapatite coating.

The coating precursors include a calcium precursor including but not limited to $Ca(C_{11}H_{19}O_2)_2$ (bis (tetramethl, heptanedionato)Calcium), $C_{10}H_2F_{12}O_4Ca$ (calcium hexflurorpentant-dionate), $C_6H_{14}O_4Ca$ (calcium methoxyethoxide) and combinations thereof, and a phosphate precursor including but not limited to $(C_2H_5O)_3PO$ (trimethylphosphate), $(C_3H_7O)_3PO$ (triethylphosphate), $(ClCH_2CH_2O)_3P(O)$ (Tris(2-chloroethyl)phosphate) and combinations thereof.

The relative amount or ratio of calcium precursor to phosphate precursor as denoted by Ca/P is within a range to deposit crystalline calcium phosphate compound. Using $Ca(C_{11}H_{19}O_2)_2$ and $(C_2H_5O)_3PO$, the Ca/P mole ratio may range from about 1.35 to about 1.65, preferably the Ca/P ratio is from about 1.45 to about 1.55. For a mole ratio outside of this range, the film becomes amorphous Calcium phosphate. For different calcium phosphate precursors, the ratio range will be different to match the stoichiometric composition.

Heating of the substrate is to a minimum temperature sufficient to decompose the precursors. Temperature above the minimum temperature may be selected for a desired surface roughness of the final coating. Generally lower temperatures provide a smoother coating surface, whereas higher temperature provide a rougher coating surface. A minimum temperature for the above mentioned precursor(s) is about 200° C.

The PEMOCVD process is generally done at a pressure below atmospheric pressure ranging from about $10^{-3}$ torr to just below atmospheric pressure. However, in the present invention, too low of a pressure results in little or no deposition of precursor onto the substrate and too high of a pressure leads to substantial contamination, especially carbon (from the precursor) contamination of the coating. Substantial contamination is an amount of impurities (especially carbon) in excess of 5 wt % of the weight of the coating. Accordingly, it has been discovered that for the present invention, the pressure should be above about 1 torr and below about 35 orr.

Once the coating is on the substrate, it may further be provided with an agent for release after implantation. The agent is selected from the group of protein, antibiotic, growth factor and combinations thereof that can be adsorbed by the coating prior to implantation.

The coating is dense and may be from 1 atom or molecule to several microns in thickness because atoms or molecules are deposited instead of particles as in the prior art. Useful coating thickness may be from 0.1 micron to 20 micron and may be less than 5 micron, less than 3 micron, or less than 1 micron.

EXAMPLE 1

An experiment was conducted to demonstrate making a calcium phosphate coating on a substrate.

The PEMOCVD system was based on Emcore's Discovery 75 Oxide System, modified to incorporate a 1.5 kW downstream microwave source for oxygen plasma, and two in-situ monitoring probes: Fourier transform IR spectrometer and multi-wavelength spectroscopic ellipsometer. The Discovery 75 design uses a cold-wall, vertical stainless steel reactor wherein the substrate is mounted on a high speed rotating disk. The substrate was heated by a molybdenum filament and the maximum temperature was about 1000° C. The PEMOCVD system has a direct liquid-source injection system with two source reservoirs. The liquid injection delivery system is particularly suitable for multicomponent coatings.

Silicon (100) wafers (1" or 2" diameter) with a thin $TiO_2$ layer (200 Å) grown onto the Si wafers were used as the substrate(s). The purpose for depositing the $TiO_2$ layer was to obtain a substrate surface similar to that of Ti alloy implants since all Ti alloy implants consist of a thin native oxide layer of Ti.

Commercially available $Ca(C_{11}H_{19}O_2)_2$ (bis (tetramethl, heptanedionato)Calcium) and $(C_2H_5O)_3PO$ (trimethylphosphate) were used as the precursors for Ca and P, respectively. Separate calcium and phosphate precursors, in desired molar amounts, were initially dissolved and diluted in solutions with a solvent. The solvent may be isopropanol, tetrahydrofuran or combinations thereof at room temperature. The preferred solvent is a mixture so that evaporation temperature is increased with the isopropanol. A 50/50 vol % mixture was used in this experiment. These two solutions at a selected ratio were delivered with a precision pump to a vaporizer heated to 230° C. The composition of calcium phosphate coatings was controlled by selecting flow rates of the precursor solutions. The Ca/P ratio was varied from 1.35 to 1.65 by controlling the flow rates of the Ca and P solutions.

The TCP coatings were deposited at temperatures from 500° C. to 650° C. at 10 torr. Growth rate and coating thickness were monitored in real time by spectroscopic ellipsometry. The growth rate was about 15 nm/min, and the thickness ranged from 0.1 $\mu$m to 1 $\mu$m. The substrate temperature and flow rates of carrier gas were varied to control the film structure, composition, and thickness uniformity.

Crystal structure determination of TCP coatings was carried out by X-ray diffraction using a Philips MPD X'pert powder diffractometer using Cu K$\alpha$ radiation. The Ca/P ratio of the coatings and oxidation state of Ca and P were analyzed by means of X-ray photoelectron spectroscopy (XPS) using PHI Quantum 2000. XPS spectra were excited by monochromatized Al K$\alpha$ radiation. Surface morphology of the coatings was characterized by scanning electron microscopy (SEM) using field-emission LEO 982.

All coatings were very smooth and mirror-like. Spectroscopic ellipsometry revealed that coatings were transparent, suggesting high crystal quality. This is consistent with the observation of color change as a function of coating thickness. SEM observations showed that no cracks were present in the coatings.

X-ray diffraction (XRD) showed that as-deposited coatings were crystalline, pure $\alpha$-TCP. No post-deposition annealing was needed to form crystalline phases. FIG. 1 shows XRD patterns of TCP coatings deposited at three different substrate temperatures. All peaks can be indexed by the Joint Committee on Powder Diffraction Standard (No. 9-348) for $\alpha$-TCP. The flat defined baseline of the spectra is indicative of a crystalline material with little or no amorphous content. The most notable difference between these spectra is related to the structural texture of the coatings.

These preferred growth orientations strongly depend on the growth temperature. The relative intensities of the peaks for the α-TCP coating deposited at 650° C. are similar to those for powder samples, showing that the α-TCP coating is randomly oriented. Strong peaks at 2θ=22.2° and 34.6° were observed for the coating deposited at 575° C., indicating that the coating was (150) and (080) oriented. Further decrease of the growth temperature to 500° C. resulted in a (060) texture, corresponding to the peak at 2θ=25.8°. Thus, homogeneous nucleation and growth occurred at 650° C., and the deposition was dominated thermodynamically. In contrast, the deposition was controlled by growth kinetics at lower growth temperatures. Different crystallographic orientations dominated grain growth at different temperatures, resulting in different textures.

Figure 2:
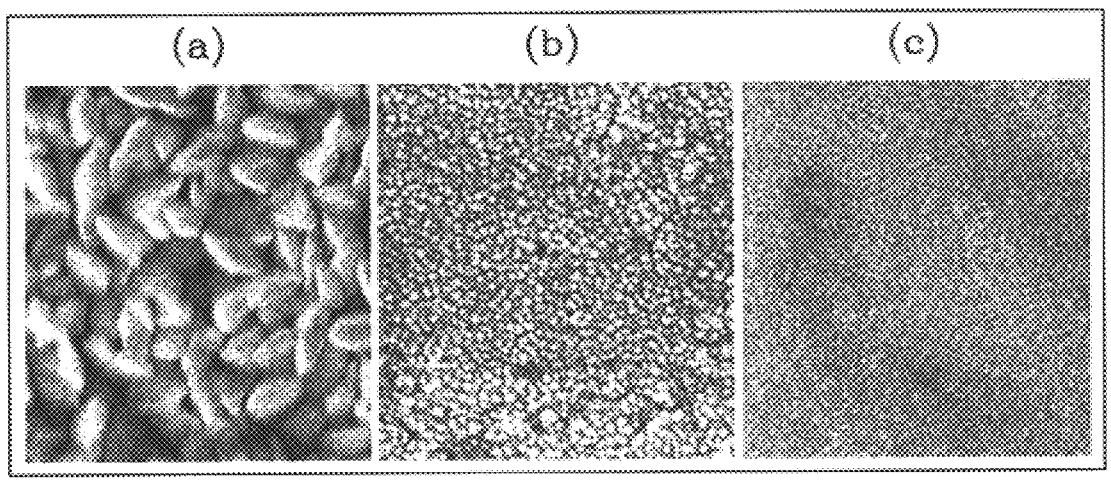
FIG. 2 is three scanning electron micrographs of the TCP coatings deposited at substrate temperatures of (a) 650° C., (b) 575° C. and (c) 500° C.

The surface morphology of the coatings was also very different and was strongly dependent on the growth temperatures as shown in FIG. 2. The grain size of the coatings decreased with decreasing growth temperature. The grain size of the TCP coating deposited at 650° C. is almost ten times larger than that at 575° C., whereas the grain size was not resolved for the coating deposited at 500° C. The results show that grain growth was much faster at higher temperatures. In addition, all three surfaces were very dense and homogenous in appearance. The thickness of the coatings was similar for a given period of growth time at the three temperatures, indicating that the nucleation rate was higher at low temperatures as compared to that at high temperature resulting in a similar thickness. Thus, the high nucleation rate and low grain growth at low temperatures resulted in dense, fine-grain microstructure, whereas the low nucleation rate and high grain growth at high temperatures leaded to dense, course-grain microstructure. Such a temperature dependence of the coating microstructure makes it possible to deposit TCP coatings with controlled surface characteristics.

Figure 3:
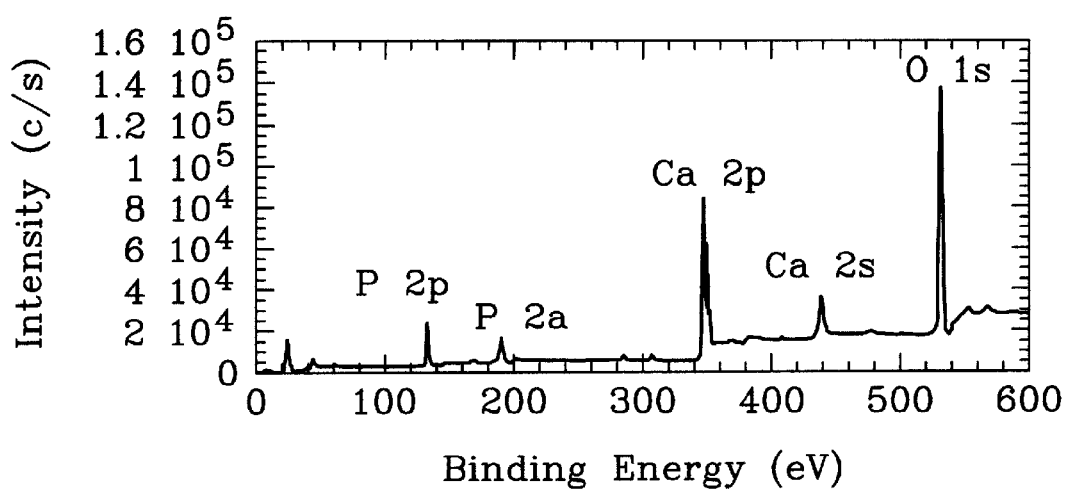
FIG. 3 is a typical XPS spectrum of the TCP coatings.

The composition of the TCP coatings was determined from Ca 3p and P 2p core-level intensities in XPS. The Ca/P ratio was calculated from the measured Ca $3P_{3/2}$ and P 2p peak areas in the same spectrum after correction for photoemission sensitivity factors. XPS revealed that the composition were very uniform across the substrates with a variation of less than 5%. FIG. 3 shows a typical XPS spectrum of the TCP coatings. It was found that the coatings with the Ca/P ratio from 1.45 to 1.55 were crystalline, α-TCP. However, the TCP coatings contained a notable amount of amorphous phase for the Ca/P ratio close to 1.45 or 1.55. In contrast, the coatings with the Ca/P ratio higher than 1.55 or less than 1.45 were complete amorphous phase.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of using a plasma-enhanced metal organic chemical vapor deposition process for coating a substrate with a calcium phosphate compound, comprising the steps of:

(a) providing a gaseous stream of a coating precursor mixture having an organic calcium precursor and a phosphate precursor;

(b) providing a plasma; and (c) contacting said gaseous stream and said plasma with a heated substrate at a minimum temperature to decompose said coating precursor mixture at a selected vacuum pressure sufficient to achieve a coating having a coating thickness of less than 5 μm and low enough to avoid substantial contamination of the coating whereupon reacting said coating precursor mixture and forming the calcium phosphate compound coating on said substrate.

2. The method as recited in claim 1, wherein said substrate is selected from the group consisting of metal, ceramic, glass and combinations thereof.

3. The method as recited in claim 2, wherein said metal is selected from the group consisting of titanium, titanium alloy, chrome molybdenum steel, stainless steel and combinations thereof.

4. The method as recited in claim 1, wherein said calcium precursor is selected from the group consisting of $Ca(C_{11}H_{19}O_2)_2$ (bis (tetramethl,heptanedionato)Calcium), $C_{10}H_2F_{12}O_4Ca$ (calcium hexflurorpentant-dionate), $C_6H_{14}O_4Ca$ (calcium methoxyethoxide) and combinations thereof.

5. The method as recited in claim 1, wherein said phosphate precursor is selected from the group consisting of $(C_2H_5O)_3PO$ (trimethylphosphate), $(C_3H_7O)_3PO$ (triethylphosphate), $(ClCH_2CH_2O)_3P(O)$ (Tris(2-chloroethyl)phosphate) and combinations thereof.

6. The method as recited in claim 1, wherein a mole ratio of Ca/P is from about 1.35 to about 1.65.

7. The method as recited in claim 1, wherein a mole ratio of Ca/P is from about 1.45 to about 1.55.

8. The method as recited in claim 1, wherein said minimum temperature is about 200° C.

9. The method as recited in claim 1, wherein said vacuum pressure is from about 1 torr to about 35 torr.

10. The method as recited in claim 1, further comprising the step of placing an agent onto the coating.

11. The method as recited in claim 10, wherein said agent is selected from the group consisting of protein, antibiotic, growth factor and combinations thereof.

12. The method as recited in claim 1, wherein the plasma is generated by a microwave source.

13. The method as recited in claim 1, wherein the plasma is an oxygen plasma.

14. The method as recited in claim 1, wherein the calcium phosphate compound coating has a density greater than or equal to 80% of theoretical density.

15. The method as recited in claim 14, wherein said thickness is less than 3 micron.

16. A method of using a plasma-enhanced metal organic chemical vapor deposition process for coating a substrate with a calcium phosphate compound, comprising the steps of:

(a) providing a gaseous stream of a coating precursor mixture having an organic calcium precursor, said calcium precursor selected from the group consisting of $Ca(C_{11}H_{19}O_2)_2$ (bis (tetramethl,heptanedionato) Calcium), $C_{10}H_2F_{12}O_4Ca$ (calcium hexflurorpentant-dionate), $C_6H_{14}O_4Ca$ (calcium methoxyethoxide) and combinations thereof, and a phosphate precursor;

(b) providing a plasma; and (c) contacting said gaseous stream and said plasma with a heated substrate at a minimum temperature to decompose said coating precursor mixture at a selected vacuum pressure sufficient to achieve a coating and low enough to avoid substantial contamination of the coating whereupon reacting said coating precursor mixture and forming the calcium phosphate compound coating on said substrate.

17. A method of using a plasma-enhanced metal organic chemical vapor deposition process for coating a substrate with a calcium phosphate compound, comprising the steps of:

(a) providing a gaseous stream of a coating precursor mixture having an organic calcium precursor and a phosphate precursor, said phosphate precursor selected from the group consisting of $(C_2H_5O)_3PO$ (trimethylphosphate), $(C_3H_7O)_3PO$ (triethylphosphate), $(ClCH_2CH_2O)_3P(O)$ (Tris(2-chloroethyl)phosphate) and combinations thereof; and (b) providing a plasma; and (c) contacting said gaseous stream and said plasma with a heated substrate at a minimum temperature to decompose said coating precursor mixture at a selected vacuum pressure sufficient to achieve a coating and low enough to avoid substantial contamination of the coating whereupon reacting said coating precursor mixture and forming the calcium phosphate compound coating on said substrate.

* * * * *